United States Patent [19]
Le et al.

[11] Patent Number: 5,486,197
[45] Date of Patent: Jan. 23, 1996

[54] TWO-PIECE SUTURE ANCHOR WITH BARBS

[75] Inventors: Thu A. Le, Matawan; Izi Bruker, Flemington; Brian H. Luscombe, Warren; Dennis D. Jamiolkowski, Long Valley, all of N.J.

[73] Assignee: Ethicon, Inc., Somerville, N.J.

[21] Appl. No.: 216,997

[22] Filed: Mar. 24, 1994

[51] Int. Cl.$^6$ ................................................ A61B 17/04
[52] U.S. Cl. .......................... 606/232; 411/80; 411/355
[58] Field of Search ............................ 606/232, 73–75; 411/41, 45, 75, 80, 355, 344

[56] References Cited

U.S. PATENT DOCUMENTS

| | | |
|---|---|---|
| D. 331,463 | 12/1992 | Rosenberg . |
| D. 331,626 | 12/1992 | Hayhurst et al. . |
| 2,587,907 | 3/1952 | Schroeder et al. ............... 411/75 |
| 4,011,602 | 3/1977 | Rybicki et al. . |
| 4,013,071 | 3/1977 | Rosenberg . |
| 4,236,429 | 12/1980 | Dolch ................................ 411/41 |
| 4,632,100 | 12/1986 | Somers . |
| 4,721,103 | 1/1988 | Feedland . |
| 4,738,255 | 4/1988 | Goble et al. . |
| 4,759,765 | 7/1988 | Kampen . |
| 4,772,286 | 9/1988 | Goble et al. . |
| 4,784,126 | 11/1988 | Hourahane . |
| 4,828,562 | 5/1989 | Kenna . |
| 4,834,752 | 5/1989 | Van Kampen . |
| 4,851,005 | 7/1989 | Hunt et al. . |
| 4,870,957 | 10/1989 | Goble et al. . |
| 4,871,289 | 10/1989 | Choiniere ........................ 411/41 |
| 4,895,148 | 1/1990 | Bays et al. . |
| 4,898,156 | 2/1990 | Gatturna et al. . |
| 4,924,865 | 5/1990 | Bays et al. . |
| 4,927,421 | 5/1990 | Goble et al. . |
| 4,968,315 | 11/1990 | Gatturna . |
| 4,979,715 | 12/1990 | Bays et al. . |
| 5,002,550 | 3/1991 | Li . |
| 5,013,316 | 5/1991 | Goble et al. . |
| 5,017,067 | 5/1991 | Ohlin ............................... 411/45 |
| 5,037,422 | 8/1991 | Hayhurst et al. . |
| 5,041,129 | 8/1991 | Hayhurst et al. . |
| 5,064,425 | 11/1991 | Branemark et al. . |
| 5,084,050 | 1/1992 | Draenert . |
| 5,102,414 | 4/1992 | Kirsch . |
| 5,108,431 | 4/1992 | Mansat . |
| 5,116,337 | 5/1992 | Johnson . |
| 5,129,906 | 7/1992 | Ross et al. . |
| 5,141,520 | 8/1992 | Goble . |
| 5,147,362 | 9/1992 | Goble . |
| 5,152,790 | 10/1992 | Rosenberg et al. . |
| 5,156,616 | 10/1992 | Meadows ........................ 606/73 |
| 5,167,665 | 12/1992 | McKinney . |
| 5,176,682 | 1/1993 | Chow . |
| 5,192,303 | 3/1993 | Gatturna et al. . |
| 5,203,784 | 4/1993 | Ross et al. . |
| 5,236,455 | 8/1993 | Hayhurst et al. ................ 606/73 |
| 5,336,240 | 8/1994 | Metzler et al. ................ 606/232 |

FOREIGN PATENT DOCUMENTS

| | | |
|---|---|---|
| 0464479 | 6/1991 | European Pat. Off. . |
| 0464480 | 6/1991 | European Pat. Off. . |
| 0504915 | 3/1992 | European Pat. Off. . |
| 0502509 | 3/1992 | European Pat. Off. . |
| 1127847 | 4/1962 | Germany ........................ 411/75 |
| 584855 | 12/1977 | U.S.S.R. ........................ 606/73 |
| WO86/03666 | 7/1986 | WIPO . |
| WO88/09157 | 12/1988 | WIPO . |

*Primary Examiner*—Gary Jackson
*Attorney, Agent, or Firm*—Joseph F. Shirtz

[57] ABSTRACT

A two-piece suture anchor is disclosed wherein a barrel-like main portion is provided with a pair of legs in a central opening. A ball-like actuating device is received within the central opening and drawn upward into the device in order to separate the legs and cause the device to expand into the soft cancellous bone of a previously prepared bone site.

15 Claims, 12 Drawing Sheets

TWO-PIECE SUTURE ANCHOR WITH BARBS

TECHNICAL FIELD

The field of art to which this invention relates is surgical implements and more specifically suture anchors for anchoring suture material to bone.

BACKGROUND ART

As the treatment of injuries to joints and soft tissue has progressed in the orthopaedic medical arts, there has been a need for medical devices which can be used to attach tendons, ligaments and other soft tissue to bone. When surgically repairing an injured joint, it is preferable to restore the joint by reattaching the damaged soft tissues rather than replacing them with an artificial material. Such restorations typically require the attachment of soft tissue such as ligaments and tendons to bone.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. In 1991, for example, there were approximately 560,000 surgical procedures performed in the United States in which soft tissue was attached to a bone in various joints including the shoulder, hip and knee.

One conventional orthopaedic procedure for reattaching soft tissue to bone is performed by initially drilling holes or tunnels at predetermined locations through a bone in sthe vicinity of a joint. Then, the surgeon approximates soft tissue to the surface of the bone using sutures threaded through these holes or tunnels. This method, although effective, is a time consuming procedure resulting in the generation of numerous bone tunnels. A known complication of drilling tunnels across bone is that nerves and other soft tissue structures may be injured by the drill bit or orthopaedic pin as it exits the far side of the bone. Also, it may be anatomically very difficult to reach and/or secure a suture/wire that has been passed through a tunnel. When securing the suture or wire on the far side of the bone, nerves and soft tissues can become entrapped and damaged.

In order to overcome some of the problems associated with the use of the conventional bone tunnel procedures, suture anchors have been developed and are frequently used to attach soft tissue to bone. A suture anchor is an orthopaedic, medical device which is typically implanted into a cavity drilled into a bone. Although less frequently, these devices have also been referred to as bone anchors. The cavity is typically referred to as a bore hole and usually does not extend through the bone. This type of bore hole is typically referred to as a "blind hole". The bore hole is typically drilled through the outer cortex layer of the bone and into the inner cancellous layer. The suture anchor may be engaged in the bore hole by a variety of mechanisms including friction fit, barbs which are forced into the cancellous layer of bone, etc. Suture anchors are known to have many advantages including reduced bone trauma, simplified application procedures, and decreased likelihood of suture failure due to abrasion on bone. Suture anchors may be used in the Bankart shoulder reconstruction for repairing the glenohumeral ligament and may also be used in surgical procedures involving rotator cuff repair and hip replacement.

Suture anchors typically have at least one suture attached. This may be by means of a hole or opening for receiving a suture or sutures. At least one end of the suture extends out from the bore hole and is used to attach soft tissue. The suture anchors presently described in the art may be made of absorbable materials which absorb over time, or they may be made from various non-absorbable, biocompatible materials. Although most suture anchors described in the art are made from nonabsorbable materials, the use of absorbable suture anchors may result in fewer complications since the suture anchor is absorbed and replaced by bone over time. In addition, the use of absorbable suture anchors may reduce the likelihood of damage to local joints caused by anchor migration.

Although suture anchors for attaching soft tissue to bone are available for use by the orthopaedic surgeon, there is a constant need in this art for novel suture anchors having improved performance characteristics.

SUMMARY OF THE INVENTION

The invention therefore includes an apparatus for holding one end of a prosthetic element such as a suture, which apparatus comprises a head and an expandable body portion which depends from said head. A wedging means is provided for expanding the body portion by relative movement between the wedging means and expandable body. The expandable body may be comprised of at least two depending legs and may further include barb means on the outer surface of the legs.

The wedging means may comprise a substantially spherical object which further defines a hole therethrough for receipt of a suture. The spherical object may ride within a passage defined by the depending legs of the body.

The internal passage defined by the depending legs may contain an internal constriction of smaller diameter than the remainder of the passageway to hold the sphere in a predetermined position once actuated or locked. Additionally, this constriction of smaller diameter may provide a tactile as well as an audible indication of the passage of the wedging means from one side of the constriction to the other, thus from an unlocked to a locked position. Preferably the passage contains a constriction which holds the wedging means in a prefired or pre-engaged position prior to spreading the legs. The suture of the suture anchor may pass along side the outside of the head or through an internal opening within the head of the body of the suture anchor. The internal surface of the legs of the suture anchor may further be shaped to partially conform to the shape of the spherical wedge when the sphere is in the seated position above the constriction described. The head may further include a stud extending therefrom for a gripping apparatus to position the suture anchor within an opening.

The invention further includes an inserter for inserting a suture anchor within an opening. The inserter cooperates with a stud extending from the suture anchor and includes an elongated section for receipt within a trocar. A distal tip of the elongated section terminates in a tubular portion which receives the stud therein. The suture is received by the suture anchor and run along side the inserter in order to hold the suture anchor in the inserter during the insertion process. Alternatively, the tubular portion may be of a diameter to provide a frictional fit with the stud. It may be preferred to have the inserter provided with an outside diameter at its elongated section which is substantially the same as the head of the suture anchor to provide a smooth transition between the two objects. Slots may be defined in the outer surface of the inserter in order to receive and protect the suture ends while the insertion process is taking place. The inserter may include an attachment mechanism for receiving and attaching at least one end of the suture to hold the suture anchor on the end of the inserter during the insertion process.

An alternative arrangement provides an inserter which is cannular in nature that allows the suture material to ride within the body of the inserter, thereby protecting it from potential damage during the placement of the suture anchor and/or during the actuation of the locking means.

BRIEF DESCRIPTION OF THE DRAWINGS

The invention will now be described with reference to the accompanying drawings wherein.

DETAILED DESCRIPTION OF THE PREFERRED EMBODIMENTS

Figure 1:
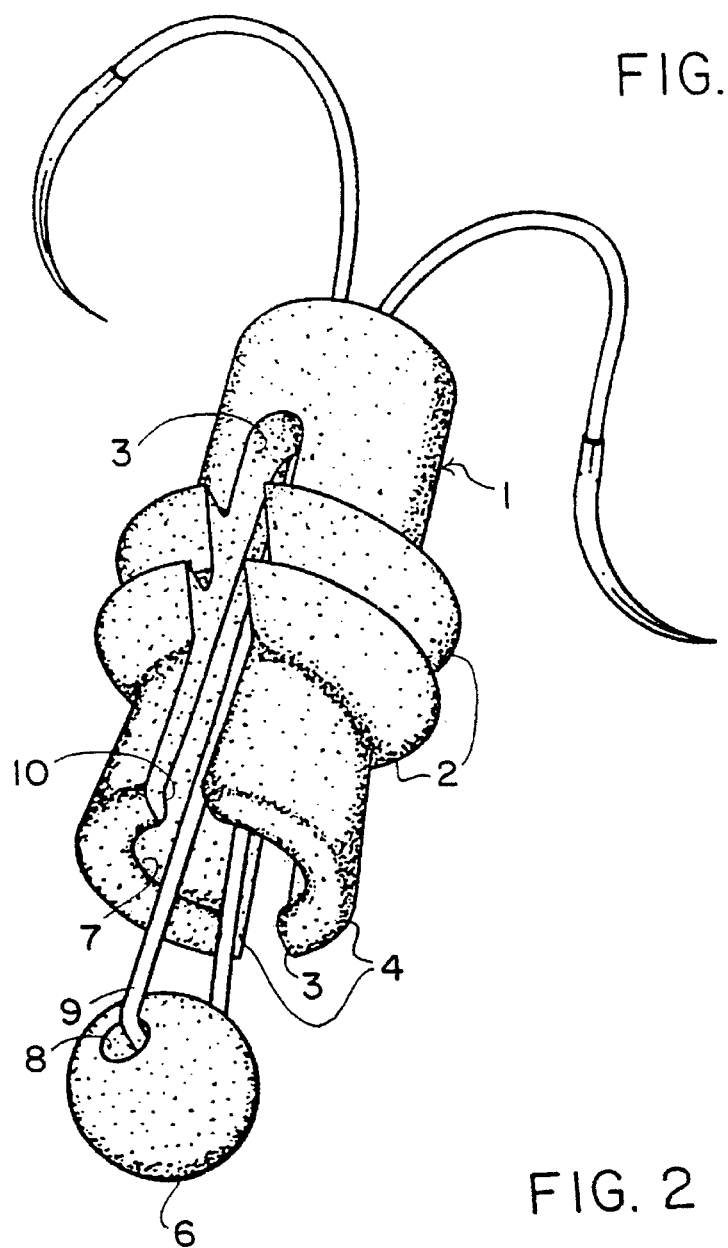
FIG. 1 is a perspective view of an embodiment of the suture anchor of the present invention in which the actuating ball has not been assembled with the anchor body.
Figure 2:
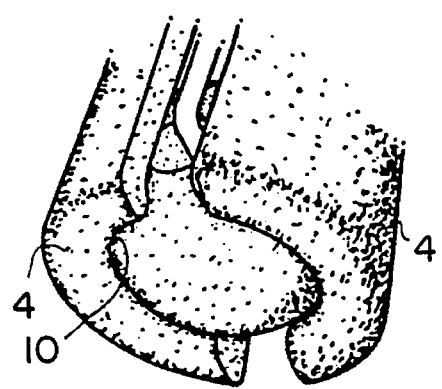
FIG. 2 is an enlarged perspective view of the suture anchor of FIG. 1 after assembly and prior to insertion into the bore hole of the bone.
Figure 6:
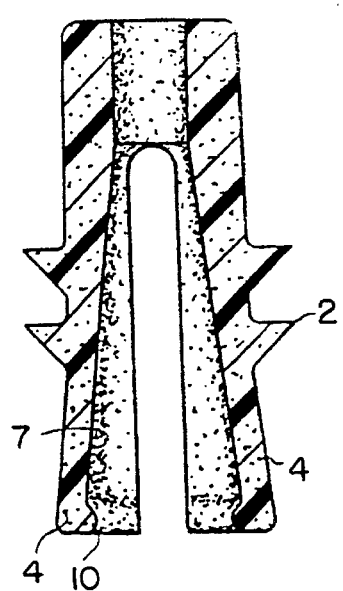
FIG. 6 is a cross-sectional view taken along line 6—6 of FIG. 3.
Figure 3:
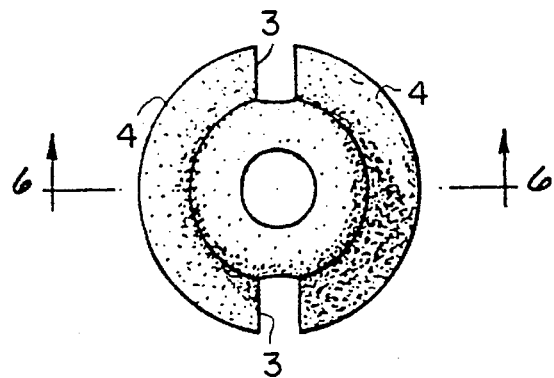
FIG. 3 is a top plan view of the body of the suture anchor of FIG. 1.
Figure 4:
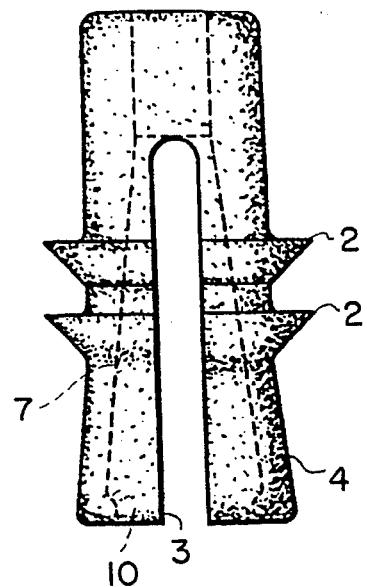
FIG. 4 is a front elevational view of the body of the suture anchor of FIG. 1.
Figure 7:
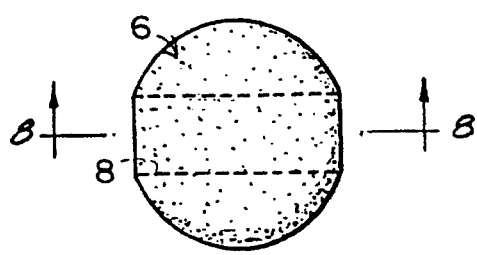
FIG. 7 is a plan view of the actuating ball of the suture anchor of FIG. 1.
Figure 8:
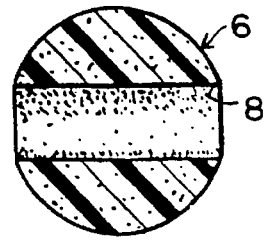
FIG. 8 is a cross-sectional view along lines 8—8 of FIG. 7.
Figure 5:
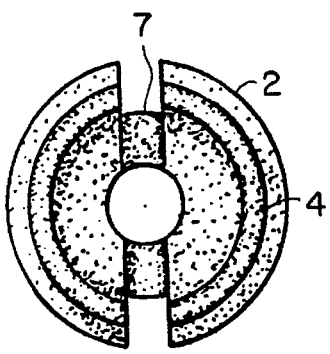
FIG. 5 is a bottom plan view of the body of the suture anchor of FIG. 1.

Referring to FIG. 1 a first embodiment of the suture anchor of the present invention is shown. The anchor has an anchor body 1 which is longitudinally extending and has radially extending fins 2. A pair of diametrically opposed slots are defined by the anchor body and extend longitudinally from one end of the anchor body to a position spaced from the second end of the anchor body. These slots 3 create a pair of legs 4 in opposed positions extending along the anchor body. A ball 6 is received within a passage 7 defined by the legs 4 of the anchor. A suture opening 8 is defined through the ball 6 to receive therein a suture 9. The ball is received within passage 7 and held in place via a radially inward extending rim 10 which causes a constriction of the opening of passage 7. The opening of passage 7 is somewhat narrower than the diameter of the ball 6 such that the ball is held within the suture anchor in the initial condition. The passage 7 extends completely through the body of the anchor as shown in FIG. 6. The suture 9 is threaded through the suture opening 8 of the ball and then both ends of the suture are in turn threaded up through the longitudinal passage 7 and out the top of the anchor through opening 7a defined in the top of the anchor.

Figure 9:
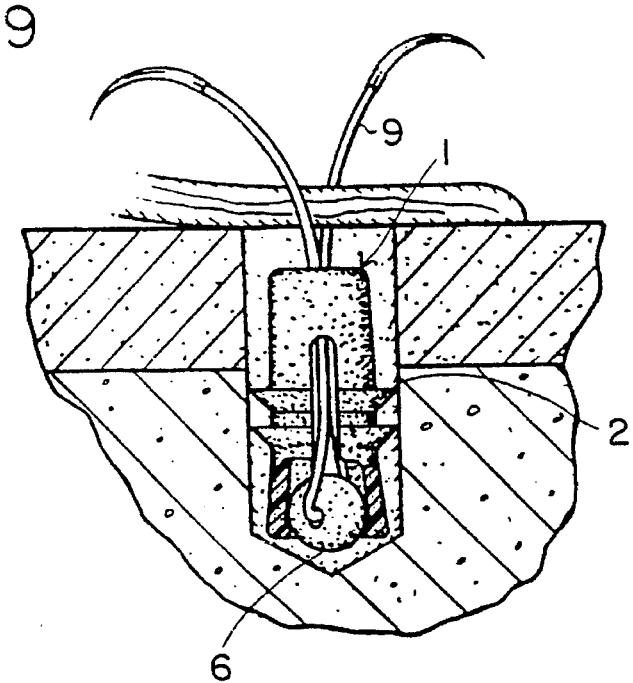
FIG. 9 is a cross-sectional view showing implantation of the suture anchor of FIG. 1 inserted into the bore hole of the bone prior to actuation.
Figure 10:
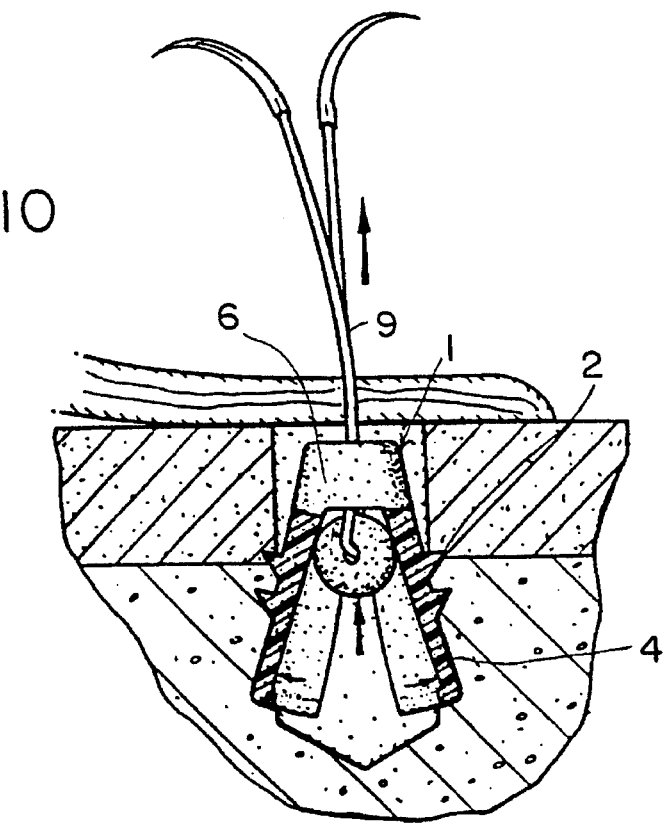
FIG. 10 is a cross-sectional view of the anchor and bone after actuation of the suture anchor of FIG. 1.

As can be seen in FIG. 6 the longitudinal passage 7 tapers towards its top end. Thus, as seen in FIG. 9 the suture anchor may be placed in an appropriate bore hole prepared in a bone site. The ball is initially held in place by the rim 10 but upon implantation within the opening of the bone, the ball is pulled upward toward the head 5 of the anchor and cooperates with the tapered inner passage to force legs 4 outward.

At this point the legs and fins 2 dig into the softer cancellous layer of the bone thus fixing the anchor in place.

Figure 11:
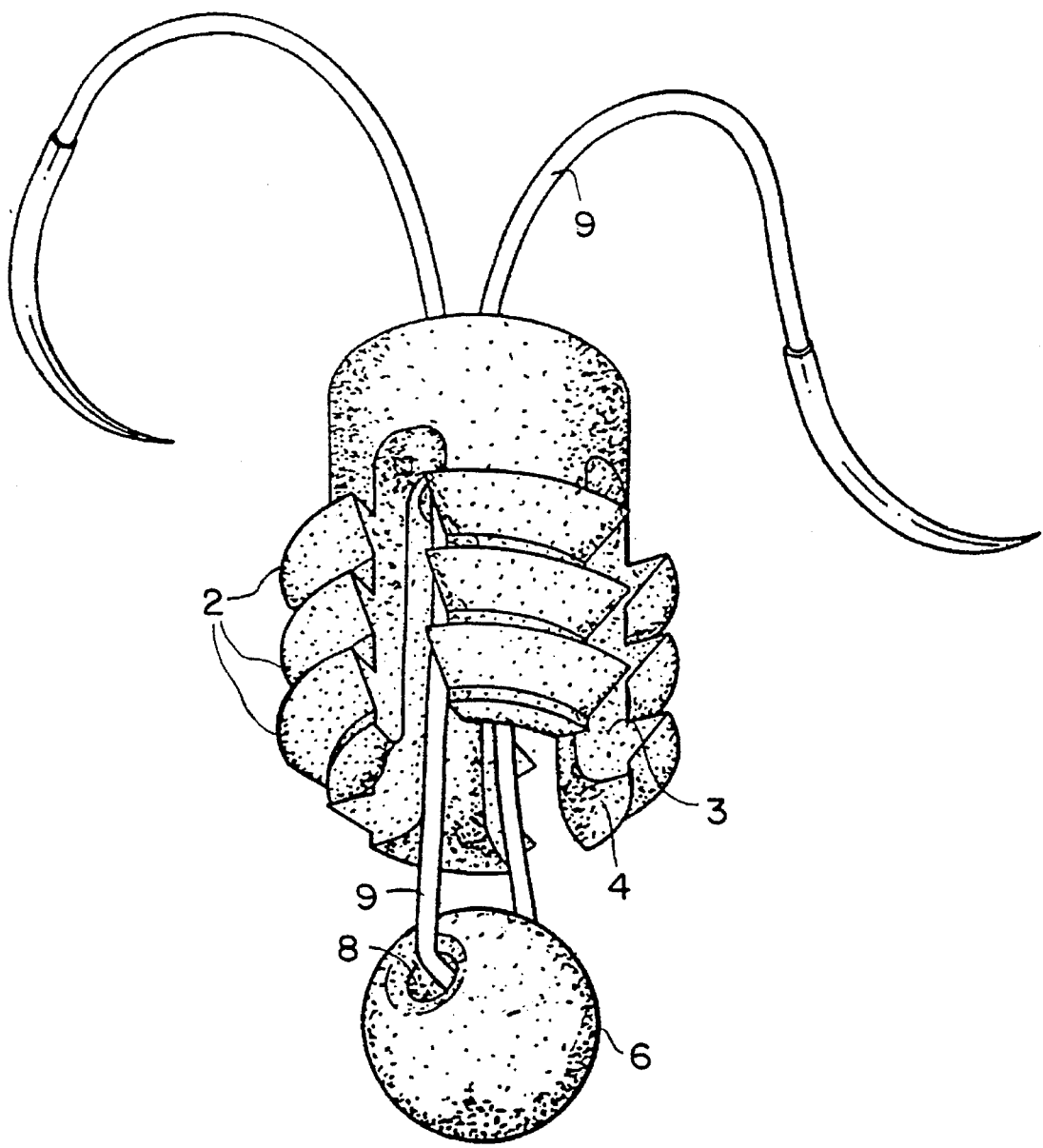
FIG. 11 is a perspective view of an alternate embodiment of the suture anchor.
Figure 12:
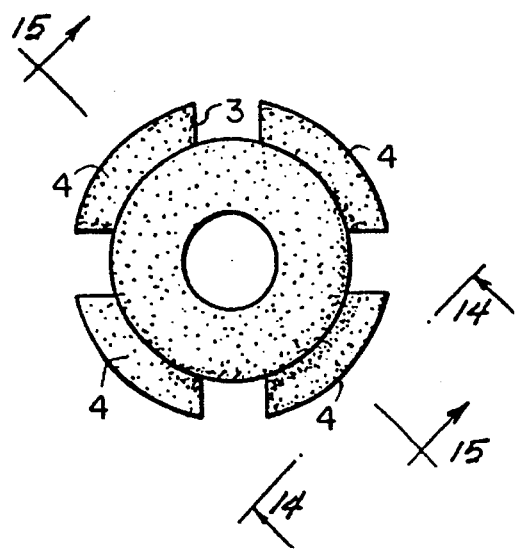
FIG. 12 is a top plan view of the body of the suture anchor of FIG. 11.
Figure 13:
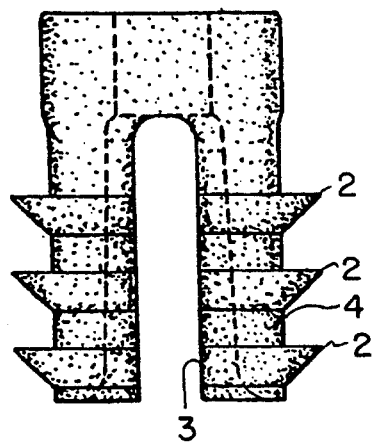
FIG. 13 is a front elevational view of the body of the suture anchor of FIG. 11.
Figure 14:
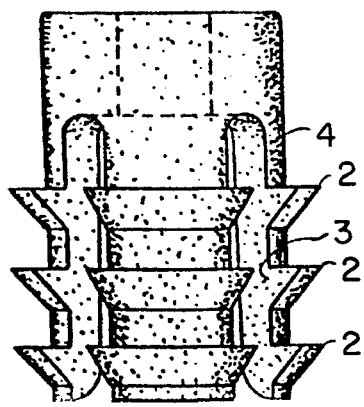
FIG. 14 is a view along lines 14—14 of FIG. 12.
Figure 15:
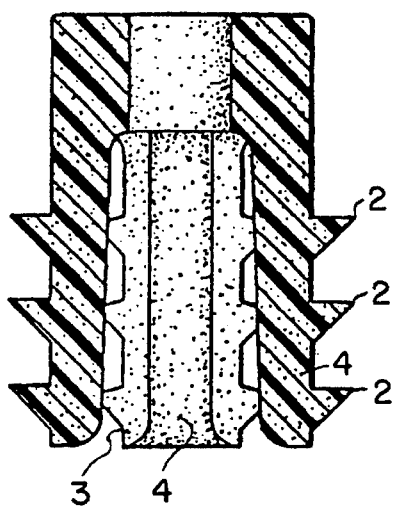
FIG. 15 is a cross-sectional view along lines 15—15 of FIG. 12.
Figure 16:
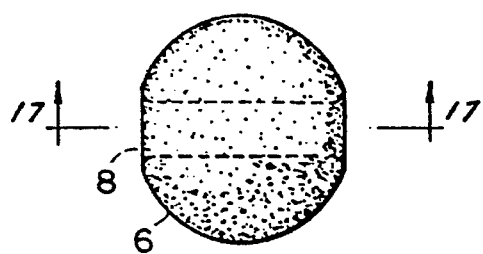
FIG. 16 is a elevational view of the actuating ball of the anchor of FIG. 11.
Figure 17:
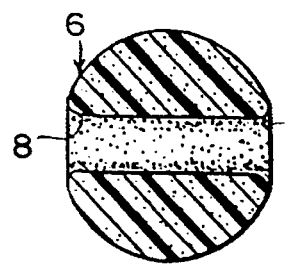
FIG. 17 is a cross-sectional view along lines 17—17 of FIG. 16.
Figure 18:
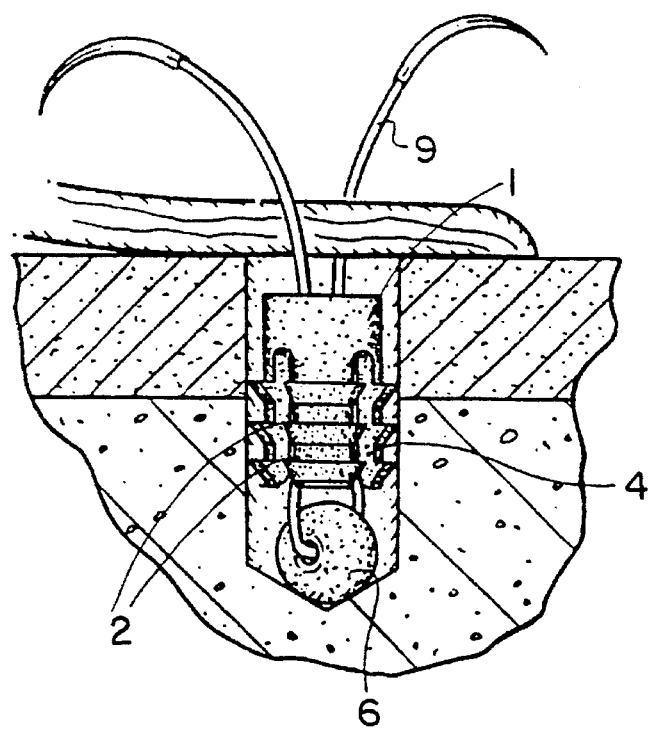
FIG. 18 is a cross-sectional view of the bone with suture anchor inserted prior to actuation.
Figure 19:
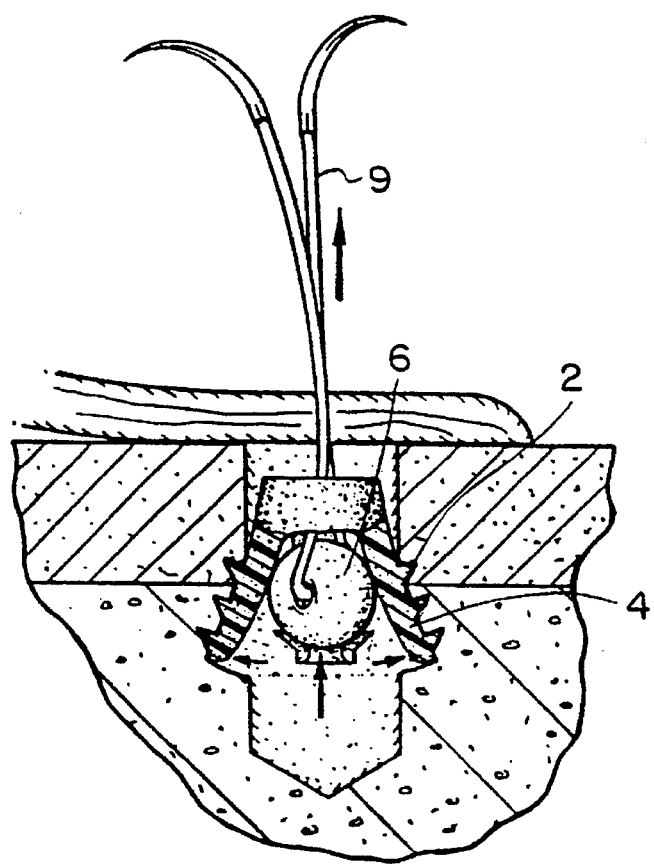
FIG. 19 shows the suture anchor of FIG. 11 after actuation.

An alternate embodiment is shown in FIG. 11. This embodiment is substantially similar to the embodiment previously described, however, it is provided with three fins instead of the two spaced radially extending fins previously described as well as having four slots 3 defined along the longitudinal portion of the anchor such that four separate legs 4 are defined thereby. Again, the central passage is tapered slightly, however, the fins extend to a position further down longitudinally along the legs 4 such that additional gripping force is provided. In this manner as seen in FIG. 18 the device may be inserted into a shallower hole whereby the movement of the ball upward causes the lower fins to dig into the soft cancellous layer of the bone.

Figure 20:
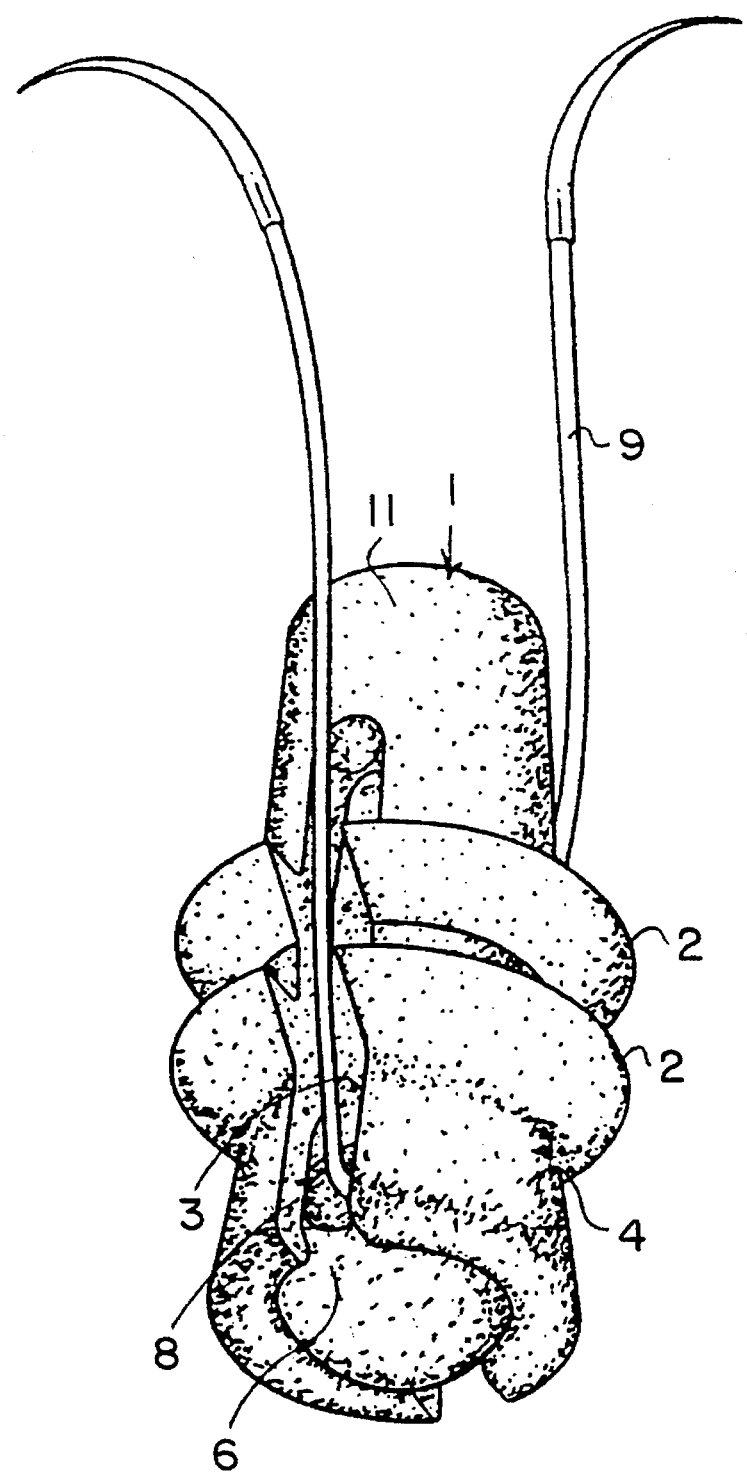
FIG. 20 is a perspective view of an alternative embodiment of the suture anchor of the present invention.
Figure 21:
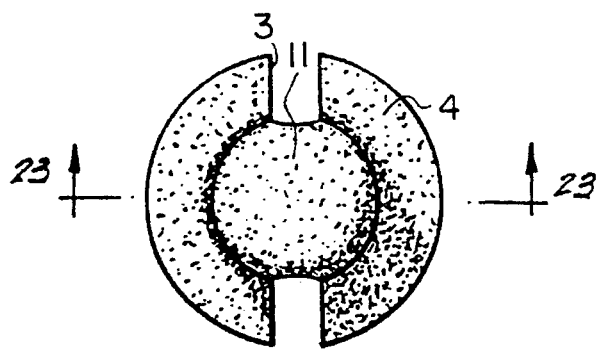
FIG. 21 is a top plan view of the body of the suture anchor of FIG. 20.

A further alternate embodiment is shown in FIG. 20. This embodiment has an anchor body 1 with fins 2 defined thereon similar to the first embodiment. A pair of slots 3 are defined along the anchor body and in turn define a pair of legs 4 extending longitudinally along the anchor body. A cap 11 which may be solid in construction is formed at one end. A ball 6 is received within a passage 7 and defines therethrough a suture opening 8. A suture 9 is received within the suture opening 8 with the ends of the suture extending through the slots and along the outside of the anchor 11. This distinguishes this anchor from the anchors previously described.

The fins 2 have a top surface 12 and a tapering bottom surface 13. The top surface 12 and the bottom surface 13 meet to form an edge 14 which will bite into the soft cancellous bone of the anchor site.

Figure 23:
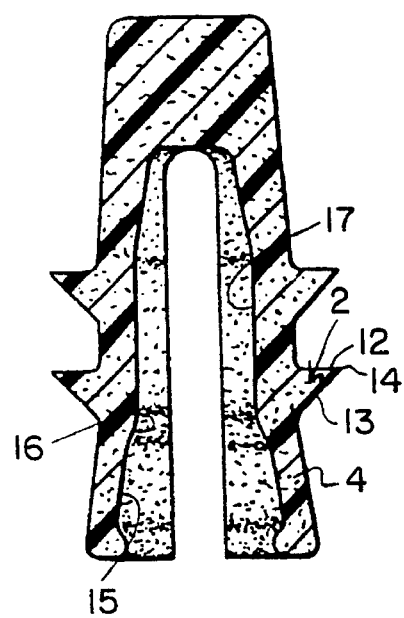
FIG. 23 is a cross-sectional view along lines 23—23 of FIG. 21.
Figure 22:
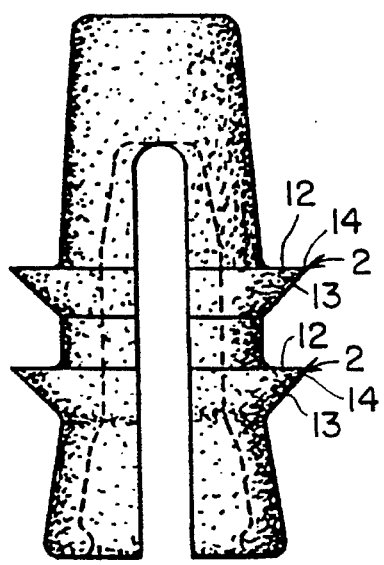
FIG. 22 is a front elevational view of the body of the suture anchor of FIG. 20.
Figure 24:
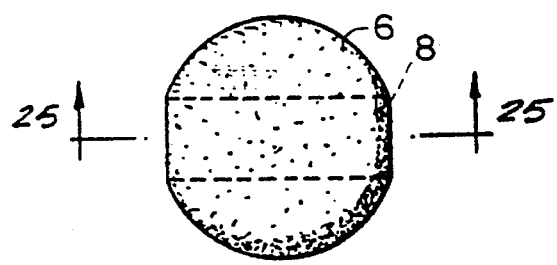
FIG. 24 is a front elevational view of the actuating ball of the suture anchor of FIG. 20.
Figure 25:
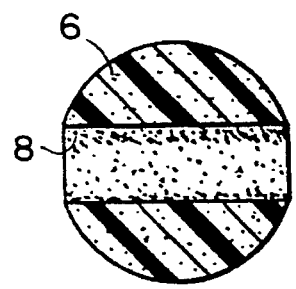
FIG. 25 is a cross-sectional view along lines 25—25 of FIG. 24.
Figure 26:
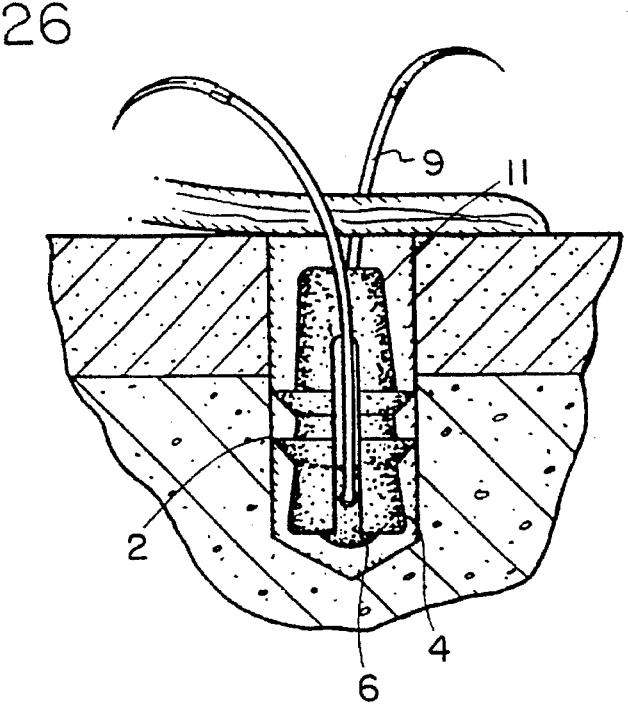
FIG. 26 is a cross-sectional view of a bone having the suture anchor inserted into a bore hole prior to actuation.
Figure 27:
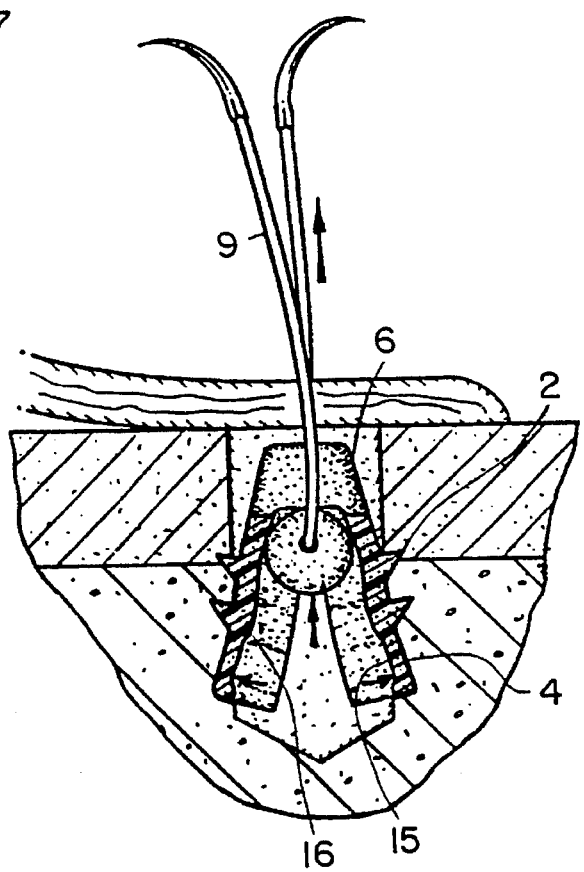
FIG. 27 is a view of the suture anchor of FIG. 26 after actuation.
Figure 28:
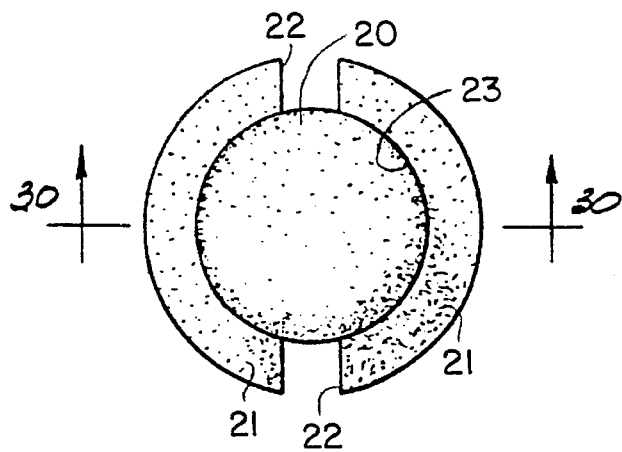
FIG. 28 is a top plan view of an alternate embodiment of the suture anchor of the present invention.
Figure 29:
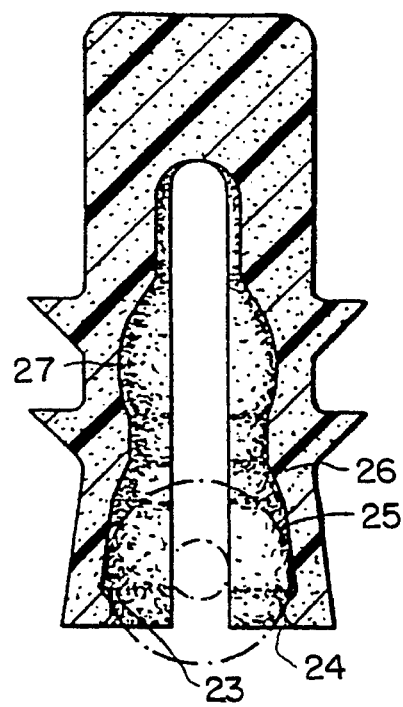
FIG. 29 is a front elevational view of the suture anchor of FIG. 28.

As is seen in FIGS. 26 and 27, an appropriate bore hole is bored through the hard outer-cortex of the bone into the soft cancellous layer beneath. The suture anchor is inserted into the opening with the ends of the suture extending through the passage in the ball along the slots and adjacent the cap of the suture. Once inserted within the bore opening, force is applied to the ends of the suture in order to draw the ball upward into the suture anchor. As is seen best in FIG. 23, a small compartment 15 is provided for seating the ball prior to actuation of the device. Upon actuation of the device, the ball is drawn upward along cam surface 16 which initiates the spreading of the legs into narrow passage 17 where the ball rests after implantation of the device.

The preferred device of the invention is shown in FIGS. 28–35. This embodiment includes an anchor body 20 which has a pair of depending legs 21 extending downward from the body. The legs 21 define a pair of slots 22 which permit expansion of the legs as will be described below. The legs in part define an inner passage 23 for receipt of an actuation ball as will be described below.

Figure 30:
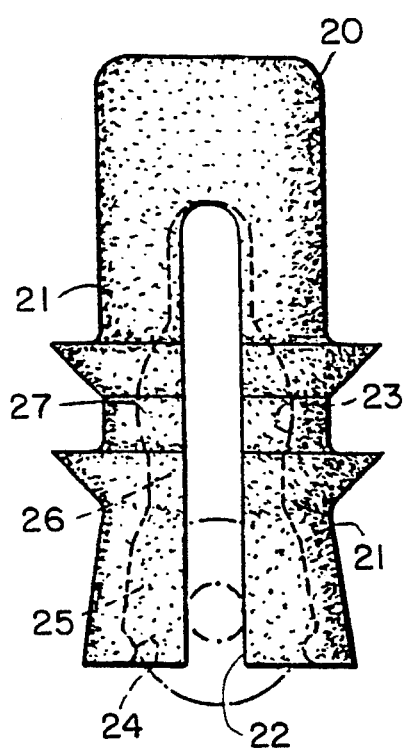
FIG. 30 is a cross-sectional view taken along lines 30—30 of FIG. 28.
Figure 31:
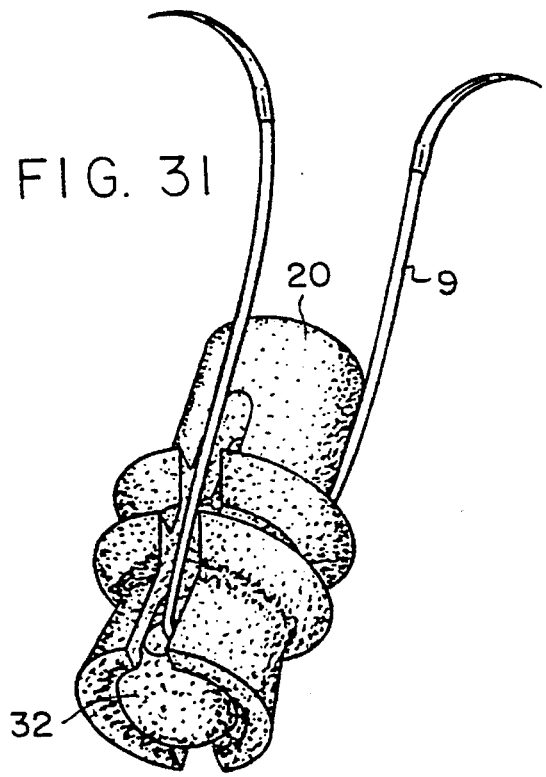
FIG. 31 is a perspective view of the suture anchor of FIGS. 28–30.
Figure 32:
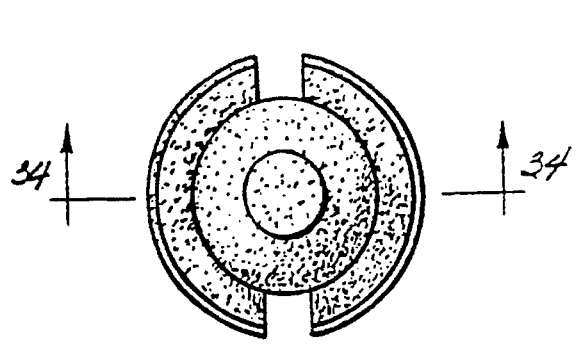
FIG. 32 is a top plan view of the most preferred suture anchor of the present invention.
Figure 34:
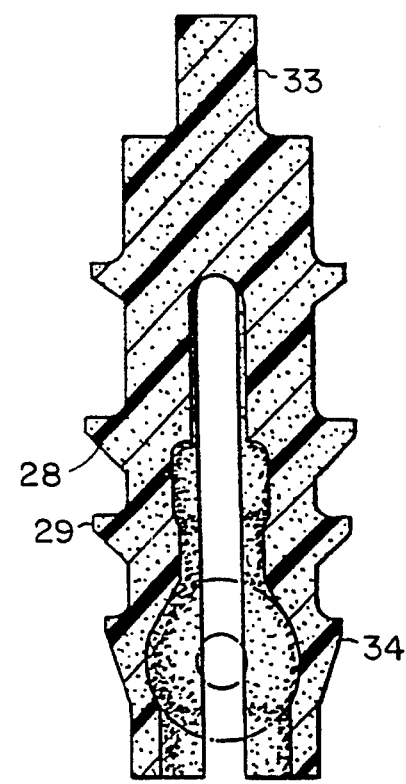
FIG. 34 is a cross-sectional view of the suture anchor of FIG. 32 taken along lines 34—34 of FIG. 32.
Figure 33:
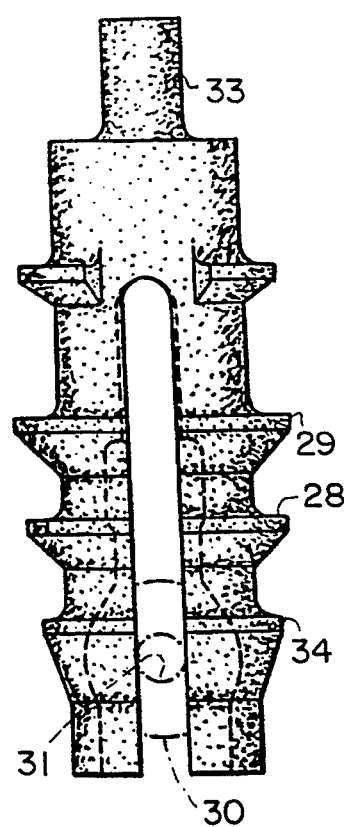
FIG. 33 is a front elevational view of the suture anchor of FIG. 32.
Figure 35:
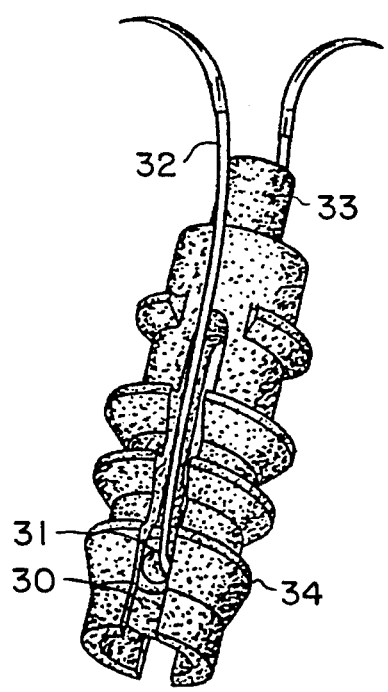
FIG. 35 is a perspective view of the suture anchor of FIGS. 32–34.

The distal opening of the inner passage 23 has a radially-extending rim 24 which adapts to hold the ball in the holding portion 25 as shown by phantom lines in FIG. 30.

A camming constriction 26 extends radially inward into the inner passage 23. This camming constriction and the remainder of the passage define a seating portion 27.

As may be seen by FIG. 30, the slots 22 extend beyond the seating portion 27. This permits passage of the suture out of the inner passage through the slots and also increases the range of motion of the legs without cracking of the legs.

The embodiment shown in FIGS. 32–35 is similar in its definition of its inner passage and camming constriction and slot, however it contains additional fins 28 which help to center the anchor within the bore hole of the bone. The bottom fin 34 actually provides a thickened portion in order to maintain the wall integrity in the area where the ball is initially seated. The ball 30 is received within this seating portion adjacent the bottom fin 34. The ball defines a suture passage 31 which receives a suture 32. The openings of the suture passage 31 are rounded slightly in order to reduce abrasion of the suture.

A stud 33 extends from the anchor body 20 in a longitudinal direction. This assists in the implantation of the device as will be described in connection with the apparatus of FIGS. 36 and 37.

The anchors of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends or other combinations thereof and equivalent thereof. Of particular utility are the polylactides, especially poly [L(-)lactide], and the lactide-rich lactide/glycolide copolymers, especially 95/5 poly [L(-)lactide-co-glycolide].

Examples of non-absorbable materials from which the suture anchors of the present invention may be made include metallic biocompatible materials including stainless steel, Nitinol, titanium, Vitalium and equivalents thereof, polymeric materials such as non-absorbable polyesters, polyamides, polyolefins, polyurethanes, and polyacetals and equivalents thereof, when metallic substances are used, then softer metals are preferred.

The suture anchor devices of the present invention, when made from an absorbable material, are preferably manufactured by molding using conventional injection molding equipment and conventional injection molding processes. A typical molding process includes the steps of (1) injecting a suitable polymer melt into an appropriately designed mold or cavity at process conditions conventionally employed for such polymer systems, (2) releasing from the mold, after the melt cools in the mold, polymer shaped in the proper configuration to meet the design criteria of the device. Additionally the anchor molded from the absorbable polymeric material, may be advantageously subjected to an annealing process to increase its mechanical or biological performance. Thermal annealing can also be used to increase the dimensional stability of molded parts by increasing the crystallinity levels in the parts. One or more surgical sutures, or one or more sutures with surgical needles attached, may be used in combination with the suture anchor and may be assembled prior to sterilization. The device can then be sterilized using conventional methods to render the anchor suitable for surgical applications.

The bonding of the anchors of the present invention to bone may be advantageously increased by promoting bone growth. This can be accomplished by having a microporous surface into which the bone can rapidly grow to aid fixation. This may be particularly advantageous in the case of a metallic anchor, especially a titanium or titanium alloy anchor, but may also provide benefit in the case of polymeric anchors of the present invention, especially those made of absorbable materials. Other methods include the coating of the anchor's surface with a substance to promote adhesion to the bone. Such coatings include the hydroxyapatite-containing-glass coatings described by Ishikawa, et al., in the article "Effect of Hydroxyapatite Containing Glass Coating on the Bonding between Bone and Titanium Implants" appearing in Clinical Materials, Volume 14, 1993, pages 277–285.

It is further noted that the anchors of the present invention can be made to contain growth factors, especially bone growth factors, that can advantageously increase the effectiveness of the anchors, especially in the area of fixation. This may be accomplished in a number of ways, including via coatings or, in the case of absorbable materials by incorporating the growth factors within the device and allowing them to diffuse out.

Figure 36:
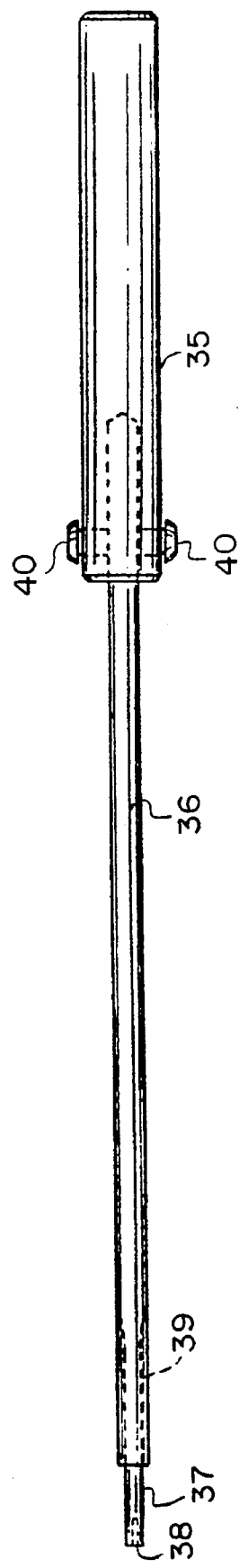
FIG. 36 is a side view of an implantation instrument for the suture anchor of FIG. 35.
Figure 37:
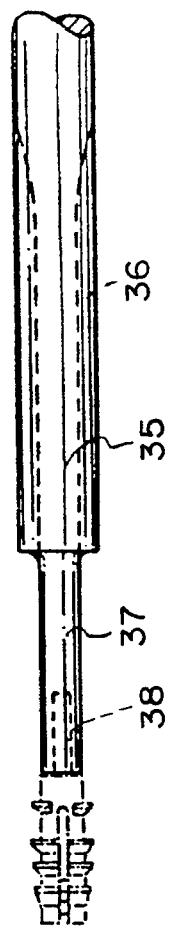
FIG. 37 is a view of the tip of the instrument of FIG. 36.

The implantation instrument for the preferred device is shown in FIG. 36. The device has a handle 35 which has extending therefrom a shaft 36. The shaft 36 terminates in a narrower holding portion 37 which is adapted to receive the stud 33 of the suture anchor within a cylindrical seat 38 defined in the tip of the holding portion. A pair of diametrically opposed relief slots 39 are provided for the passage of the suture from the anchor along the shaft. That is, the suture is received within the suture passage defined in the ball and extends outward from the anchor and along the shaft of the apparatus. The suture, as it extends along the shaft of the apparatus, is received within the relief slots 39 and extends upward to the cleats 40 which extend from either side of the handle 35. Thus, in use, the stud of the suture anchor is received within the cylindrical seat 38. An appropriate suture extends through the suture passage of the ball and is laid along the relief slots 39 and attached to the cleats 40 thus holding the anchor in place. In an open procedure or an arthroscopic procedure, the anchor is inserted into a previously bored hole in the bone of the recipient. Once in place in the bored hole the suture is detached from the cleats and upward force is applied to the suture while keeping the anchor in place drawing the ball into the seating portion of the anchor. The action of drawing the ball into the seating portion forces the legs outward as the ball passes the camming constriction and causes the legs and fins to dig into the softer cancellous bone. Thus the suture anchor is implanted within the bore and prepared for attachment of soft tissue to the bone.

The invention has been described with reference to its preferred embodiments, however, it is understood that changes may be made to the invention without departing from the spirit of the disclosure provided herein.

We claim:

1. An apparatus for holding a suture comprising
a head;
an expandable body extending distally from said head comprising at least two legs; and, wedging means for expanding said body by proximal relative movement of said wedging means within said expandable body comprising a substantially spherical object defining a hole therethrough for receipt of a suture and a suture received within said hole passing beyond said head to permit gripping of said suture for movement of said wedging means.

2. The apparatus according to claim 1 wherein said legs further include barb means on an outer surface of said legs.

3. The apparatus according to claim 1 wherein said head further defines an opening for passage of said suture therethrough.

4. The apparatus according to claim 1 further including an internal passageway defined at least in part by said depending legs and an internal constriction of smaller diameter than the remainder of said passageway to hold said sphere in a predetermined position.

5. The apparatus according to claim 4 wherein said constriction is at a distal end of said legs in order to hold said sphere in a pre-load position prior to spreading said legs.

6. The apparatus according to claim 7 further including a second constriction defined by the inner surface of said legs in a second position spaced longitudinally from said first constriction in order to hold said sphere at a distal position urging said legs into a spread position.

7. The apparatus according to claim 4 wherein said internal constriction of smaller diameter is shaped to provide entry of the wedging means through resistance to movement of the wedging means follwed by a release of said resistance to provide a tactile indication of the movement of said sphere from a first position to said predetermined position.

8. The apparatus according to claim 7 wherein said internal constriction of smaller diameter is shaped to provide an audible indication of movement of said sphere from a first position into said predetermined position.

9. The apparatus according to claim 1 further defining at least two openings for passage of said suture therethrough to extend said suture alongside said head.

10. The apparatus according to claim 1 further including a stud extending from said head for gripping said apparatus during implantation.

11. A suture anchor for receipt within an opening defined by the bone comprising a head portion having extending distally therefrom at least two expandable leg portions, said leg portions defining an internal passageway of nonconstant cross-sectional dimension;
a spherical expanding means for receipt within said passageway and having a diameter larger than said passageway to spread said legs upon movement of said sphere within said passageway toward said head; an opening defined by said sphere and a suture received therethrough, having ends of said suture passing beyond the head of said anchor to permit gripping of said suture for movement of said spherical expanding means.

12. The suture anchor according to claim 11 wherein said head defines an opening for passage of the ends of said suture from said sphere through said head.

13. The suture anchor according to claim 11 wherein said leg portions define at least one opening for passage of said suture along the outside of said head.

14. The suture anchor according to claim 11 wherein said suture includes at least one needle extending from an end of said suture.

15. The apparatus according to claim 1 wherein less than one-half of said wedging means extends beyond a distal end of said at least two legs.

* * * * *